(12) United States Patent
Hörnig

(10) Patent No.: US 8,496,380 B2
(45) Date of Patent: Jul. 30, 2013

(54) MEDICAL RADIOLOGICAL DEVICE AND RADIOLOGICAL SYSTEM

(75) Inventor: Mathias Hörnig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 328 days.

(21) Appl. No.: 12/918,909

(22) PCT Filed: Jan. 23, 2009

(86) PCT No.: PCT/EP2009/050740
§ 371 (c)(1),
(2), (4) Date: Aug. 23, 2010

(87) PCT Pub. No.: WO2009/106391
PCT Pub. Date: Sep. 3, 2009

(65) Prior Publication Data
US 2011/0004347 A1    Jan. 6, 2011

(30) Foreign Application Priority Data

Feb. 26, 2008  (DE) .......................... 10 2008 011 157

(51) Int. Cl.
*A61B 6/08* (2006.01)
(52) U.S. Cl.
USPC .......................................... 378/205

(58) Field of Classification Search
USPC ............................................................ 378/37
See application file for complete search history.

(56) References Cited

U.S. PATENT DOCUMENTS

| 5,930,328 | A  | * | 7/1999  | Nakamura et al. ............. 378/91 |
| 6,891,920 | B1 | * | 5/2005  | Minyard et al. ................. 378/37 |
| 7,302,032 | B2 | * | 11/2007 | Akagi ............................. 378/37 |
| 2007/0232881 | A1 |  | 10/2007 | Shai et al. |
| 2007/0291897 | A1 | * | 12/2007 | Ramsauer et al. ............. 378/37 |

FOREIGN PATENT DOCUMENTS

| WO | WO2006/027341 A1 | * | 3/2006 |
| WO | WO 2006/061357 A1 |  | 6/2006 |

* cited by examiner

*Primary Examiner* — Irakli Kiknadze
*Assistant Examiner* — Danielle Fox
(74) *Attorney, Agent, or Firm* — Schiff Hardin LLP

(57) ABSTRACT

A medical radiological system has a radiological device with at least one element that can be electrically adjusted in order to allow an adaptation of the radiological device to body dimensions of a patient to be examined. The radiological device has a controller with an interface that receives a patient parameter set from a computer, with which patient data are processed and stored. The controller calculates a desired position of the element from the received patient data set, and automatically controls positioning of the element by electrically adjusting the element to the desired position.

5 Claims, 2 Drawing Sheets

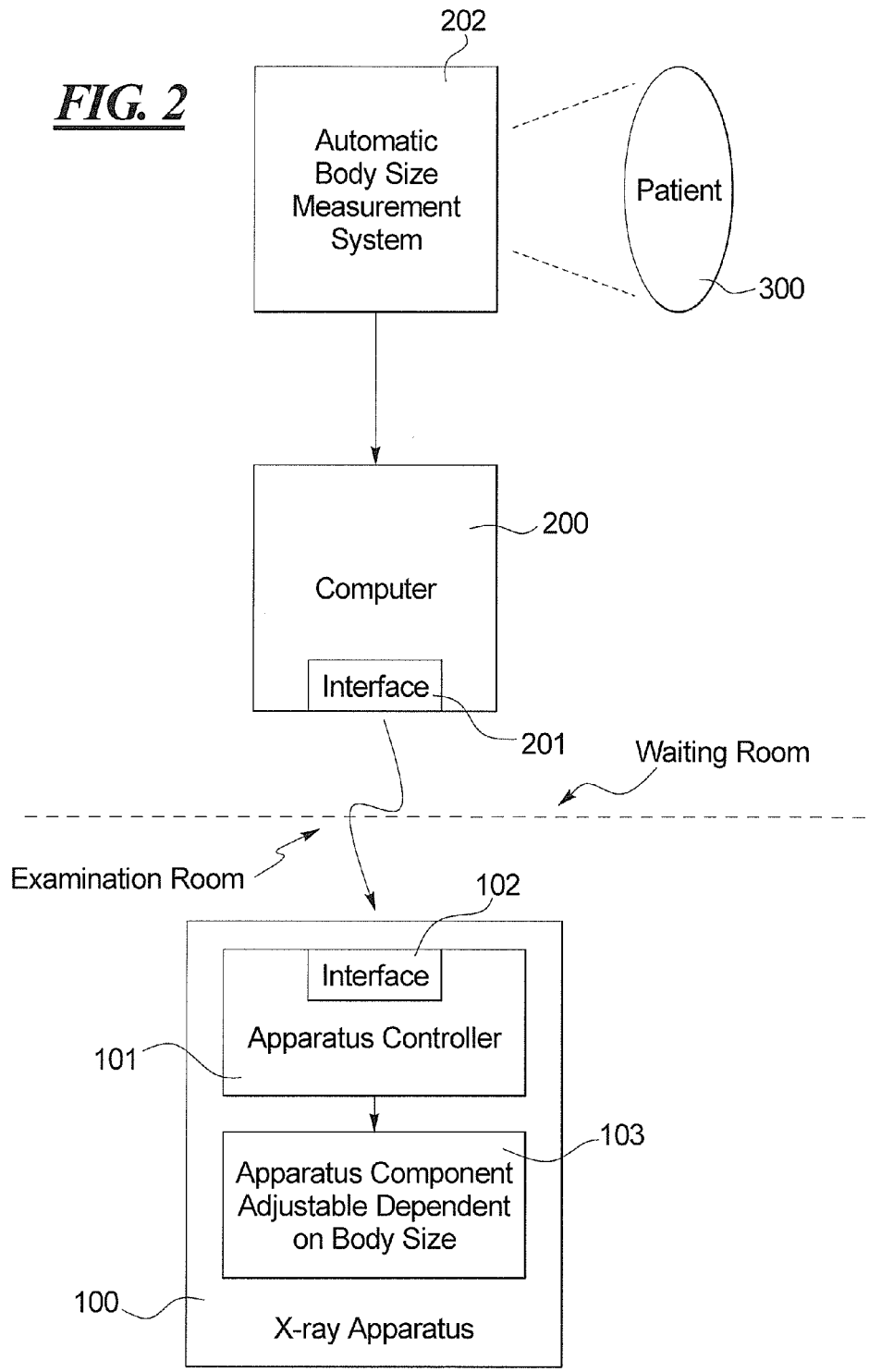

MEDICAL RADIOLOGICAL DEVICE AND RADIOLOGICAL SYSTEM

BACKGROUND OF THE INVENTION

1. Field of the Invention

The present invention concerns a medical x-ray system. In particular, the present invention concerns an improved medical x-ray system with an x-ray apparatus with at least one element that is electrically adjustable in order to enable an adaptation of the x-ray apparatus to body measurements of a patient to be examined.

2. Description of the Prior Art

Medical x-ray apparatuses serve to establish anomalies in the body. X-ray radiation emitted by an x-ray radiator thereby penetrates a body part to be examined and is absorbed by an electronic sensor or suitable film material and is subsequently evaluated. The body part to be examined thereby most often lies on a table which simultaneously incorporates the sensor or a film cartridge.

Elements of an x-ray apparatus—for instance the radiation source and the table—are frequently adjustable in order to enable an examination of patients of different sizes with the x-ray apparatus. These adjustments are made manually by an assistant or a physician to be examined. During this time the apparatus is not otherwise functional and the assistant or physician is also occupied only with the adjustment of the x-ray apparatus. It is the case that patients are excited frequently, whereby the adjustment is additionally hindered.

SUMMARY OF THE INVENTION

It is an object of the invention to provide a medical x-ray apparatus and an x-ray system that reduce the scope of the adjustments (that still must be made manually) of adjustable elements of the x-ray apparatus.

This object is achieved in accordance with the invention by a medical x-ray apparatus with at least one element that is electrically adjustable in order to enable an adaptation of the x-ray apparatus to body measurements of a patient to be examined. The x-ray apparatus has a controller with:

an interface that receives a patient parameter set from a computer with which patient data are processed and stored;

a calculator unit that calculates a desired position of the element from the received patient parameter set; and a control unit that automatically sets the electrically adjustable element to the desired position.

The object is also achieved by an x-ray system having such an x-ray apparatus and a computer with which patient data—in particular an electronic patient file—are processed and stored, and having the following:

an extractor unit that extracts a patient parameter set from the patient data; and an interface that transfers the patient parameter set and a control command to the medical x-ray apparatus, this control command initiating the automatic control of the electrically adjustable element in the desired position.

An advantage of the present invention is that an x-ray apparatus according to the invention can be integrated into an x-ray system according to the invention that is subsequently automatically adjusted, matching the respective patient, without action by an assistant or physician. In the simplest case, for example, the height of the patient is electronically extracted from the electronic patient file, transmitted to the x-ray apparatus as a patient parameter set and there converted into a desired position of an element (for example height of a table).

DESCRIPTION OF THE DRAWING

FIG. 2 schematically illustrates a medical system in accordance with the invention, embodying a medical x-ray apparatus as shown in FIG. 1.

FIG. 1 shows a medical x-ray apparatus 100, such as a mammography x-ray apparatus (for example). X-ray apparatus 100 has a stationary stand element 110 to which a support element 120 is attached so as to be height-adjustable. The height adjustment of the support element 120 ensues by means of an electrical motor in the stand element 110 and serves to adapt the x-ray apparatus to different body sizes of patients. The examination of both standing and sitting patients is thereby possible.

DESCRIPTION OF THE PREFERRED EMBODIMENTS

Figure 1:
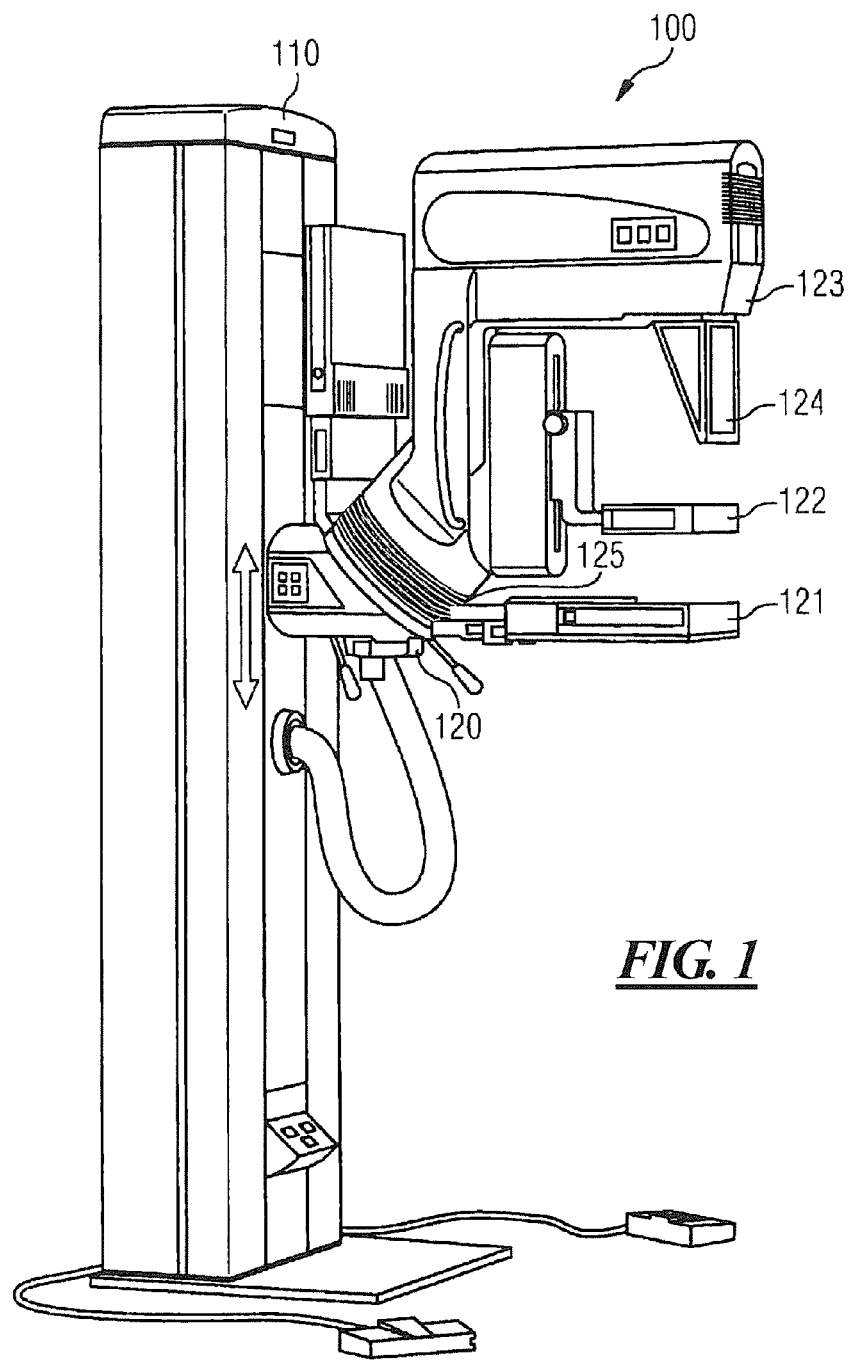
FIG. 1 schematically illustrates a medical x-ray apparatus constructed and operating in accordance with the present invention.

The single figure shows a medical x-ray apparatus 100, such as a mammography x-ray apparatus (for example). X-ray apparatus 100 has a stationary stand element 110 to which a support element 120 is attached so as to be height-adjustable. The height adjustment of the support element 120 ensues by means of an electrical motor in the stand element 110 and serves to adapt the x-ray apparatus to different body sizes of patients. The examination of both standing and sitting patients is thereby possible.

Support element 120 supports a table 121 that supports the body part to be examined and has a digital x-ray sensor or, respectively, a film cartridge (not shown). An optional plate 122 (likewise attached to the support element 120) serves for fixing and/or shaping the body part to be examined. Support element 120 also supports an apparatus 123 generating x-rays (designated more simply as a radiation source in the following). Table 121 and radiation source 123 are thereby attached to the support element 120 such that they are aligned relative to one another in a manner suitable for image generation.

Through a joint 125, support element 120 provides the possibility to rotate the entire structure (table 121 and radiation source 123) in a motorized manner, for instance in order to rotate the beam axis (formed by table 121 and radiation source 123) by 45° and thus to enable a slanted, lateral accommodation of the organ to be examined.

In the shown x-ray apparatus 100, the elements "table 121" and "radiation source 123" are executed so as to be electrically adjustable in order to enable an adaptation of the x-ray apparatus to different body sizes of patients, and are thus examples of the component 103 shown in FIG. 2. This adaptation is classically made by an assistant or physician while the patient is already standing restlessly in front of the x-ray apparatus. This requires time and intensifies the patient's anxiousness since the adjustment takes place only slowly due to the sensitivity and the mass of the device and the required precision.

According to the invention as shown in FIG. 2, a patient parameter set is transmitted to the x-ray apparatus 100 via wired wireless interfaces 102 and 201 of a controller 101 of the x-ray apparatus 101 and a computer 200. From this patient parameter set the controller 101 of the x-ray apparatus determines a desired setting of the adjustable elements 121, 123 and suitably controls the corresponding actuators in order to achieve this desired position.

In one exemplary embodiment shown in FIG. 2, the patient parameter set includes the body size of the patient which is either learned from an electronic patient file or is determined in a waiting room as shown in FIG. 2, that is separated from the examination room via an automatic measurement system 202. An adjustment of the table height is therefore approximately possible in any case so that readjustments that are possibly still necessary can be carried out quickly by the assistant or physician who is required anyway for the image acquisition.

For example, a system which possesses multiple light barriers that are advantageously arranged equidistantly atop one another can be used as an automatic measurement system 202. To measure a patient, the patient is positioned in the light barrier region and the size of the patient 300 is determined from the interrupted light barriers.

Alternatively, the size of a patient 300 can be determined automatically by means of a camera, wherein the image of the patient 300 is compared (controlled by a program) with reference images in order to determine the size of the patient 300. Given the use of a camera, other size parameters can additionally be determined; for example, the height and/or position of the breast for a mammography examination instead of or in addition to the size of the patient 300.

By repeated examinations, a position of elements 121, 123 that has determined to be optimal by the assistant or physician is adopted in the electronic patient file. The x-ray apparatus 100 has operating means for this purpose, with which the operator communicates to the apparatus that the current position is the optimal position. This current position (or the parameters characterizing this position) is thereupon determined by the controller; a corresponding patient data set is generated from this which in turn is transferred wirelessly or via wires to a computer which stores the electronic patient file. Given a re-examination of the patient 300, the optimal settings can henceforth be accessed so that the x-ray apparatus 100 automatically brings the elements 121, 123 into the optimal position after registration of the patient for the examination while patient 300 and assistant or physician conduct other examination steps.

In the event that the size of the patient is not present in the electronic patient file and cannot be recorded before the x-ray examination, in exemplary embodiments the age of the patient (for example) are used for an approximate presetting of the adjustable elements 121, 123. Additional details can additionally or alternatively be considered, for instance that an examination takes place while sitting, for example because the patient cannot stand.

In addition to the height of the table 121, further adjustments must occasionally be made, for instance the alignment of a shield 124, the position of adjustable elements relative to one another (for instance the distance between radiation source 123 and table 121) etc. These additional parameters can be stored with the patient parameter set in the electronic patient file without further measures.

It is possible—in particular for larger medical facilities with many examination stations—to additionally use the parameters and settings obtained at a first examination station to preset the following (x-ray) examination apparatuses in the examination workflow. For this purpose it is sufficient for suitable parameters to be determined at the first examination station and stored in the electronic patient file, which parameters then serve to set adjustable elements at the following (x-ray) examination apparatuses.

Although modifications and changes may be suggested by those skilled in the art, it is the intention of the inventor to embody within the patent warranted heron all changes and modifications as reasonably and properly come within the scope of his contribution to the art.

I claim as my invention:

1. A medical x-ray system comprising:
a medical x-ray apparatus comprising at least one element that is electrically adjustable in order to enable adaptation of the x-ray apparatus to a body size of a patient to be examined;
an automatic measurement system configured to automatically interact with the patient to be examined to make a measurement of the body size of the patient to be examined and, from said measurement, to generate data representing the body size of the patient;
a computer in communication with said measurement system to receive said data representing the body size of the patient therefrom, said computer being configured to store and process patient data of said patient, including said data representing the body size of the patient, to generate a patient parameter set for operating said medical x-ray apparatus to interact with said patient, said computer having a computer interface;
said medical x-ray apparatus comprising a controller having a controller interface, in communication with said computer interface, that receives said patient parameter set from the computer;
said controller being configured to calculate a desired position of the at least one electrically adjustable element from the received patient parameter set; and
said controller being configured to automatically set the at least one electrically adjustable element to the desired position.

2. Medical x-ray system according to claim 1, wherein the at least one electrically adjustable element is selected from the group consisting of a patient table, a detector table, a bucky tray table and a radiation source.

3. Medical x-ray system according to claim 1, wherein the automatic measurement system operates optically.

4. An x-ray system as claimed in claim 1 wherein said medical x-ray apparatus is a medical imaging x-ray apparatus.

5. A medical x-ray system as claimed in claim 4 wherein said medical imaging apparatus is a mammography apparatus.

* * * * *